United States Patent [19]

Adams

[11] 3,950,510

[45] Apr. 13, 1976

[54] CONDITIONING SHAMPOO CONTAINING A WATER-INSOLUBLE HAIR COSMETIC AGENT

[75] Inventor: Geoffrey Philip Adams, Addlestone, England

[73] Assignee: Lever Brothers Company, New York, N.Y.

[22] Filed: July 25, 1973

[21] Appl. No.: 382,440

[30] Foreign Application Priority Data

Aug. 1, 1972 United Kingdom............... 35901/72
Feb. 5, 1973 United Kingdom................. 5571/73

[52] U.S. Cl. ......... 424/70; 252/DIG. 3; 252/DIG. 4; 252/DIG. 13; 252/119; 252/544; 252/547; 252/554; 424/DIG. 2; 424/78; 424/81; 424/359; 424/71; 424/363; 424/365
[51] Int. Cl.².......................................... A61K 7/06
[58] Field of Search... 252/DIG. 3, DIG. 4, DIG. 13, 252/119, 152, 544, 545, 547, 554; 424/DIG. 2, 70, 71, 81, 78, 363

[56] References Cited
UNITED STATES PATENTS

| 1,516,820 | 11/1924 | Johnson et al................. | 424/363 X |
|---|---|---|---|
| 2,128,973 | 9/1938 | Tisdale et al. .................. | 424/363 X |
| 2,519,062 | 8/1950 | Miskel et al. ................... | 252/119 X |
| 2,711,397 | 6/1955 | Owen et al.......................... | 252/152 |
| 2,931,802 | 4/1960 | Touey et al........................ | 260/234 |
| 3,098,794 | 7/1963 | Dohr et al............................ | 424/70 |
| 3,580,853 | 5/1961 | Parran ............................. | 424/70 X |

FOREIGN PATENTS OR APPLICATIONS 1,396,482  3/1965  France............................... 424/365

OTHER PUBLICATIONS

Chemical Abstracts, Vol. 44: 11134c, (1950).

*Primary Examiner*—Sam Rosen
*Assistant Examiner*—Vera C. Clarke
*Attorney, Agent, or Firm*—Kenneth F. Dusyn; Arnold Grant

[57] ABSTRACT

A shampoo which imparts various cosmetic attributes to the hair, ranging from gloss and condition to body and manageability comprises an aqueous solution of a surfactant and a hair cosmetic agent, for example a wood rosin or a polyketone resin maintained in dispersion in the solution by means of a thickening and suspending agent. On dilution of the shampoo with water during shampooing, the hair cosmetic agent is deposited onto the hair.

4 Claims, No Drawings

CONDITIONING SHAMPOO CONTAINING A WATER-INSOLUBLE HAIR COSMETIC AGENT

This invention relates to a shampoo composition.

In U.S. Pat. No. 3,313,734 there are described shampoos which impart body, manageability and wave-set retention effects to the hair. These shampoos contain resinous polyethyleneimines which are solubilized in a special detergent system so that when the shampoo is diluted with water during shampooing the resin is precipitated onto the hair.

However, when we examined the shampoos described we found that the water-soluble polymeric materials deposited onto the hair tended both to dull the hair and adversely affect its feel.

It is an object of the present invention to provide a shampoo depositing cosmetic agents onto the hair during shampooing to achieve various cosmetic effects varying from gloss and conditioning to body and wave-set retention without the above-described disadvantages.

In accordance with the invention there is provided a shampoo for imparting cosmetic effects to the hair comprising an aqueous solution of a surfactant and a water-insoluble hair cosmetic agent having a softening point below 50°C, maintained in dispersion in the solution by means of a thickening and suspending agent, the hair cosmetic agent being deposited onto the hair upon dilution of the shampoo during shampooing.

The nature of the hair cosmetic agent is not critical. Amongst the materials which can be used are wood rosins, polymeric resins and other resinous materials, waxes and oils. When rosins and polymeric resins are used, the cosmetic attributes imparted to the hair are generally those of body and set retention, whereas when waxes or oils are used they tend to impart gloss and to improve the condition of the hair.

When the term wood rosin is used it is intended to include not only wood rosin itself, sometimes called pine rosin, but also modified wood rosins, for example polymerized, hydrogenated, isomerized, disproportionated, esterified or etherified wood rosins. Preferred rosins are described in pamphlets entitled "Wood Rosins, Modified Rosins and Related Resins" and "Hercolyn D the Hydrogenated Methyl Ester of Rosin", published by the Hercules Powder Company.

Some specific examples of resinous materials which can be used in the shampoos of the invention are sucrose acetate isobutyrate, polyvinyl ethyl ether resins, alkyd resins, polyketone resins, vinyl acetate resins, acrylic resins and hydrocarbon resins. Substantially water-insoluble fluoropolymers can also be used.

Examples of waxes and oils are lanolin alcohols, ethoxylated higher fatty alcohols, cetylated castor oil, silicone oil, mineral and vegetable oils such as olive oil, and corn oil.

Of the above materials the preferred ones are wood rosins, sucrose acetate isobutyrate, polyketone resins, acrylic resins and hydrocarbon resins and mixtures thereof.

Two specific wood rosins which we have found particularly suitable for use in this invention are Poly-Pale (Trade Mark) E70D, a glycerol ester of a polymerized wood rosin and Hercolyn D (Trade Mark) and mixtures thereof.

By varying the softening point of the hair cosmetic agent between about 0° and 50° it is possible to impart various cosmetic attributes to the hair. Using an agent having a softening point close to the lower limit, improved condition and gloss can be obtained whereas when using a harder agent the hair is given greater body and manageability. Shampoos providing manageability and body can generally be formulated using hair cosmetic agents having a softening point of about 35°C, which is the preferred temperature. (When hair has "body" it appears fuller, thicker, is easier to control and more able to take and hold a set than hair which does not have body.)

The method of determining softening points which is adopted for the purposes of this specification is described in the pamphlet entitled Wood Rosins, Modified Rosins and Related Resins already referred to.

Reverting to the last example given, Hercolyn D is a liquid and Poly-Pale is a hard material (softening point 117°C), and so in order to obtain a rosin having a softening point in the preferred range it is necessary to use a mixture having a high proportion of Hercolyn. However in addition to softening hard rosins using softer rosins it is possible to soften them using oily substances such as mineral oils and organic oils, for example n-butyl oleate.

The hair cosmetic agent should be present in the shampoos of the invention in an amount of from about 1 to 25 percent by weight, preferably about 1 to 20 percent and most preferably from about 1 to 15 percent by weight of the composition.

As described above in the shampoos of this invention the hair cosmetic agent is maintained in dispersion by means of a thickening and suspending agent.

The use of a thickening and suspending agent is an important feature of the present invention. It is insufficient to employ a substance which merely thickens the aqueous solution without imparting some structure and thixotropy to it also. It is well known in the art that some substances, for example carboxylated acrylic polymers such as the Carbopols (Trade Mark) of BF Goodrich Company, the Texicryls (Trade Mark) of Scott Bader and Co Ltd and the Viscalex (Trade Mark) thickeners of Allied Colloid Corporation impart structure and thixotropy to the liquid which contains them as well as thickening it. Put another way, these thickeners impart a high yield value to solutions containing them. The concept of yield value and its relationship to that of viscosity is discussed in the pamphlet "Carbopol Water-Soluble Resins", published by BF Goodrich Chemical Company particularly pages 12 to 17. It is this type of thickening and suspending agent which is to be used in the compositions of this invention.

Without wishing to be limited to any particular theory, it is generally believed that those thickening agents which also impart suspending properties, structure and a degree of thixotropy to a solution do so because the constituent polymer molecules are charged, and hydrogen bonding is set up between the polymer molecules and water. The hair cosmetic agent is maintained in dispersion by virtue of the structure imparted to the liquid. When this structure is broken down by dilution of the shampoo the hair cosmetic agent is deposited onto the hair.

The amount of thickening and suspending agent required in the composition will be dependent upon the nature and amount of the hair cosmetic agent in the shampoo. It will also be dependent upon the viscosity which is required in the final shampoo composition. However this amount will generally be from about 0.2 to 5%, preferably 0.5 to 2% by weight.

Particularly when hair cosmetic agents having a softening point close to 50°C are used the shampoo compositions of this invention may require the use of a hair lubricant to provide ease of combing and anti-stat properties to the hair after use of the shampoo. The hair lubricant may be solubilized in the surfactant solution or present as an additional layer.

When solubilized in the composition, the lubricant can be present in an amount of from about 0.5 to about 10 weight percent, based on the weight of the total composition; when insoluble, forming a separate phase, it is preferred to increase the upper limit to about 25 weight percent with a desired range being from about 4 to about 20 weight percent.

Examples of such lubricants include organic oils, for example esters such as cetyl palmitate, n-butyl oleate, isopropyl myristate and adipates, glycol polysiloxanes and mineral oil, and mixtures thereof.

As implied above the shampoo compositions may be constituted as a multi-phase system, as described in U.S. Pat. No. 3,533,955.

The shampoos of this invention comprise one or more surfactants. Salts of sulphonated and sulphated anionic surfactants are preferred, and in particular the sodium, magnesium, ammonium, mono-, di- and triethanolamine salts of sulphated $C_{12}$–$C_{21}$ fatty alcohols and such salts of the sulphonated $C_{12}$–$C_{21}$ alkylaryl compounds. Typical anionic detergents include lauryl sulphates, lauryl ether sulphates and dodecylbenzene sulphonates.

Suitable nonionic surfactants include fatty acid alkanolamides such as lauric diethanolamide, coconut mono- and di- ethanolamide and lauric isopropanolamide and ethylene and propylene oxide condensates of hydrophobic bases such as long chain fatty alcohols, alkylphenols or fatty acid alkanolamides. Examples of cationic surfactants which can be included in the shampoos of this invention in minor proportions are cetyl trimethyl ammonium chloride and alkyl dimethyl benzyl ammonium chloride.

Preferably the surfactant is present in an amount of from about 5 to about 60 percent, preferably from about 7 to about 40 percent and most preferably from about 10 to about 30 percent by weight of the composition. Compositions containing lower amounts of surfactant than this do not clean the hair well and also give low foam volumes, while those containing greater amounts introduce problems of eye irritancy.

Optionally, the shampoo may also contain from about 0.2 to about 15 percent by weight, or more, usually 0.5 to 5 percent by weight of one or more lather boosters and/or stabilizers, to increase sudsing power and foam stability. Examples of these include coco amide, lauric diethanolamide, lauric isopropanolamide, coconut monoethanolamide, betaines and sulphobetaines. Soaps of alkali metals, such as sodium and potassium decanoate and laurate may also be added to the shampoo in order to increase the viscosity of the foam produced during use.

The shampoo composition may, of course, also include if desired such further additives as perfumes, essential oils or dyes to enhance and improve the commercial acceptability of the product.

The remainder of the composition usually comprises water.

The following examples illustrate shampoo compositions in accordance with the present invention.

The hair cosmetic agents shown in Table 1 were incorporated into a base shampoo having the following composition.

|  | % by weight |
|---|---|
| Ammonium lauryl sulphate | 18.0 |
| Lauric isopropanolamide | 1.0 |
| $^k$Carboxylated acrylic copolymer (thickening and suspending agent) | about 1.0 |
| Hair cosmetic agent of Table 1 | 1.0 to 12.0 |
| Colour | 0.5 |
| Perfume | 0.5 |
| Water | balance to 100 |

The amount of the thickening and suspending agent in the shampoo was adjusted according to the nature of the hair cosmetic agent so that the viscosity of the shampoo was from 500 to 2,500 cps.

The pH of the shampoo ws adjusted to 6.5 or greater.

Table 1

| Example No. | Hair Cosmetic Agent | % by weight in base shampoo |
|---|---|---|
| 1 | Ethoxylated lanolin | 2.0 |
|  | Glycerol monostearate | 2.0 |
| 2 | *Long chain fatty condensate | 5.0 |
|  | Glycerol monostearate | 2.0 |
| 3 | Olive oil | 1.0 |
| 4 | Olive oil | 2.0 |
| 5 | Lanolin alcohol | 3.0 |
|  | Ethylene glycol monostearate | 1.0 |
| 6 | Lanolin alcohol | 4.0 |
|  | Ethylene glycol monostearate | 1.0 |

*The long chain fatty condensate was an "Alcamine" resin supplied by Allied Colloids Ltd, Low Moor, Bradford, Yorks, England.

A second series of compositions was formulated by incorporating the hair cosmetic agents shown in Table 2 into the above base shampoo.

Table 2

| Example No. | Hair Cosmetic Agent | % by weight |
|---|---|---|
| 7 | Sucrose acetate isobutyrate | 5.0 |
|  | $^a$Polyketone resin | 1.0 |
| 8 | $^b$Lipopeptide | 4.0 |
|  | $^c$Vinyl alcohol-vinyl acetate resin | 8.0 |
| 9 | Dimethyl hydantoin-formaldehyde resin | 1.0 |
|  | Sucrose acetate isobutyrate | 5.0 |
| 10 | $^d$Hydrocarbon resin | 3.3 |
|  | Sucrose acetate isobutyrate | 6.7 |
| 11 | $^e$Silicone oil 46,000 cps | 5.0 |
| 12 | $^e$Silicone oil 143,000 cps | 5.0 |
| 13 | $^d$Hydrocarbon resin | 3.3 |
|  | n-butyl oleate | 6.7 |
| 14 | $^d$Hydrocarbon resin | 3.3 |
|  | Corn oil/mineral oil mixture | 6.7 |
| 15 | $^g$Acrylic resin | 10.0 |

A third series of compositions, which contained wood rosins as the cosmetic agent had the following formulations:

|  | Percent by Weight Example 16 |
|---|---|
| Ammonium lauryl sulphate | 18.0 |
| $^h$Hydrogenated methyl ester of refined pine rosin | 5.0 |
| $^j$Polymerised refined pine rosin ester | 1.0 |
| n-Butyl oleate | 1.0 |
| $^k$Carboxylated acrylic copolymer | 1.2 |

-continued

| | Percent by Weight Example 16 |
|---|---|
| Lauric isopropanolamide | 1.0 |
| Coconut diethanolamide | 1.0 |
| Perfume | 0.2 |
| Colouring | 0.2 |
| Water | 71.4 |
| Total | 100.0 |

The softening point of the above mixture of rosins is 35°C.

| | Percent by Weight Example 17 |
|---|---|
| Triethanolamine lauryl sulphate (40%) | 40.0 |
| hHydrogenated methyl ester of refined pine rosin | 6.0 |
| Dimerised rosin | 3.0 |
| kCarboxylated acrylic copolymer | 5.6 |
| Perfume | 0.2 |
| Colouring | 0.2 |
| Water | 45.0 |
| | 100.0 |

The pH of the shampoo was adjusted to 7.5 using ammonia solution.

| | Percent by Weight Example 18 |
|---|---|
| Triethanolamine lauryl sulphate (40%) | 45.0 |
| Hydrogenated methyl ester of refined pine rosin | 10.0 |
| Ethanol | 15.0 |
| Carboxylated acrylic copolymer | 5.6 |
| Perfume | 0.2 |
| Colouring | 0.2 |
| Water | 24.0 |
| Total | 100.0 |

The composition was adjusted to pH 7.5 using ammonia solution.

| | Percent by Weight Example 19 |
|---|---|
| Triethanolamine lauryl sulphate (40%) | 40.0 |
| hHydrogenated methyl ester of refined pine rosin | 9.0 |
| Polymerised rosin | 6.0 |
| kCarboxylated acrylic copolymer | 5.6 |
| Lauric isopropanolamide | 1.0 |
| Perfume | 0.2 |
| Colouring | 0.2 |
| Water | 39.0 |
| Total | 100.0 |

| | Percent by Weight Example 20 |
|---|---|
| Triethanolamine lauryl sulphate (40%) | 40.0 |
| hHydrogenated methyl ester of refined pine rosin | 9.0 |
| Hydrogenated rosin | 6.0 |
| kCarboxylated acrylic copolymer | 4.0 |
| Perfume | 0.2 |
| Colouring | 0.2 |
| Water | 40.6 |
| Total | 100.0 | aThe polyketone resin was ZKMA supplied by Union Carbide Corporation
eThe lipopeptide was "Lamepon LPO", an alcohol-soluble lipopeptide condensa- -continued tion product of collagen hydrolysate and oleic acid supplied by Chemische Fabrik Grunau, West Germany
fThe vinyl alcohol-vinyl acetate resin was BA-28-18 supplied by Union Carbide Corporation
gThe hydrocarbon resin was Hercules AR65 supplied by the Hercules Powder Company
iThe silicone oils were dihydroxypolysiloxanes supplied by Imperial Chemical Industries Ltd, England
jThe hydrocarbon resin was Hercules A130 supplied by the Hercules Powder Company
lThe acrylic resin was Carboset 515, supplied by BF Goodrich & Co
hThe hydrogenated methyl ester of refined pine rosin was Hercolyn D, supplied by the Hercules Powder Company
jThe polymerized refined pine rosin ester was Poly-Pale E70D also supplied by the Hercules Powder Company
kThe carboxylated acrylic copolymer was Texicryl 13-300 which is an emulsion of the polymer available from Scott Bader & Co Ltd, England "Lamepon", "Carboset", "Alcamine", "Hercolyn", "Poly-Pale" and "Texicryl" are trade marks.

That a proportion of the hair cosmetic agent in the shampoo is deposited onto hair can be demonstrated by extracting a sample of the hair with petroleum spirit, evaporating the spirit and weighing the residue.

The cosmetic attributes imparted by the shampoos described above can be assessed subjectively using the following general procedure.

A total of 20 heads of hair are washed by five skilled salon operators. Half of the head is washed with the test shampoo and the other half with a control. The control is a commercial shampoo sold under the trade mark "Sunsilk" in the United Kingdom, or, when the test shampoo is a two-phase product, a duophase shampoo sold in the USA under the trade mark "Twice as Nice".

After the washing procedures each half of each head is assessed for various attributes such as gloss, condition, body and wave-set retention using a point scoring system. The results are treated statistically to determine the dominant characteristic(s) of the test shampoo.

The shampoos described in Tables 1 and 2 were assessed for the cosmetic attributes which they imparted to the hair in the following ways.

First, switches of hair were washed in the shampoo, dried and photographed under an electron microscope. Deposits of the hair cosmetic agents could be clearly seen adhering to the hair.

Secondly, the switches were assessed subjectively for amount of deposition (an experienced operator can judge from the appearance of a switch whether and to what extent deposition has occurred), gloss, condition, ease of combing and degree of set retention.

All of the shampoos in the above examples and tables deposited a hair cosmetic agent onto the switch. The shampoos in Table 1 were considered to improve the gloss, condition and ease of combing of the hair. Those in Examples 7, 8, 13 and 14 of Table 2 were considered to impart light set-retention effects and those in the remaining examples of Table 2 to impart a high degree of set retention to the hair. All of the shampoos in Table 2 provided some degree of body also.

Of those shampoos which contained wood rosins those in Examples 16, 17, 19 and 20 imparted bodying effects to the hair, whilst that of Example 18 imparted a conditioning effect.

What is claimed is:

1. An aqueous shampoo composition for imparting cosmetic effects to the hair comprising:

a. about 5 to about 60% by weight of an anionic surfactant, a cationic surfactant, a nonionic surfactant, or a mixture thereof, and
b. about 1 to 15% by weight of a water-insoluble hair cosmetic agent consisting of wood rosin, maintained in dispersion in the composition by means of from 0.5 to 2% by weight of a thickening and suspending agent.

2. An aqueous shampoo composition for imparting cosmetic effects to the hair comprising:
a. about 5 to about 60% by weight of an anionic surfactant, a cationic surfactant, a nonionic surfactant, or a mixture thereof, and
b. about 1 to about 15% by weight of a water-insoluble hair cosmetic agent consisting of sucrose acetate isobutyrate, maintained in dispersion in the composition by means of from 0.5 to 2% by weight of a thickening and suspending agent.

3. An aqueous shampoo composition for imparting cosmetic effects to the hair comprising:
a. about 5 to about 60% by weight of an anionic surfactant, a cationic surfactant, a nonionic surfactant, or a mixture thereof, and
b. about 1 to about 15% by weight of a water-insoluble hair cosmetic agent consisting of dihydroxypolysiloxane oil, maintained in dispersion in the composition by means of from 0.5 to 2% by weight of a thickening and suspending agent.

4. An aqueous shampoo composition for imparting cosmetic effects to the hair comprising:
a. about 5 to about 60% by weight of an anionic surfactant, a cationic surfactant, a nonionic surfactant, or a mixture thereof, and
b. about 1 to about 15% by weight of a water-insoluble hair cosmetic agent consisting of mineral oil, maintained in dispersion in the composition by means of from 0.5 to 2% by weight of a thickening and suspending agent.

* * * * *